United States Patent [19]

Imamura et al.

[11] Patent Number: 4,568,835
[45] Date of Patent: Feb. 4, 1986

[54] APPARATUS FOR DETECTING FOREIGN MATTERS ON A PLANAR SUBSTRATE

[75] Inventors: Kazunori Imamura, Tokyo; Akikazu Tanimoto; Nobutoshi Abe, both of Kawasaki, all of Japan

[73] Assignee: Nippon Kogaku K.K., Tokyo, Japan

[21] Appl. No.: 438,468

[22] Filed: Nov. 2, 1982

[30] Foreign Application Priority Data

Nov. 6, 1981 [JP] Japan ............................. 56-178091

[51] Int. Cl.$^4$ ........................................... G01N 21/88
[52] U.S. Cl. ..................................... 250/572; 356/446
[58] Field of Search ............... 250/562, 563, 571, 572; 356/335–343, 430–431, 445–446; 358/293

[56] References Cited

U.S. PATENT DOCUMENTS 2,604,809  7/1952  Mitchell ............................. 356/446
4,423,331 12/1983  Koizumi et al. ..................... 250/572

FOREIGN PATENT DOCUMENTS 2643361  3/1978  Fed. Rep. of Germany ...... 356/446

OTHER PUBLICATIONS

Klochko et al., "Photometric Method of Estimating the Particle Size of Carbon Black", Industrial Laboratory, vol. 39, No. 5, pp. 753–755, May '73.

Primary Examiner—Edward P. Westin
Attorney, Agent, or Firm—Fitzpatrick, Cella, Harper & Scinto

[57] ABSTRACT

An apparatus for detecting foreign matter present on a planar substrate comprises apparatus for scanning the surface of the substrate with an oblique incident light beam, apparatus for photo-electrically detecting the scattered light generator in the trajectory of the light beam scanning on the substrate, and apparatus for eliminating stray light unnecessary for the foreign matter detection.

9 Claims, 7 Drawing Figures

APPARATUS FOR DETECTING FOREIGN MATTERS ON A PLANAR SUBSTRATE

BACKGROUND OF THE INVENTION

1. Field of the Invention

The present invention relates to an apparatus for detecting foreign matter such as small dust particles present on a test specimen by means of the scattering phenomenon of a laser beam or the like, and more particularly to an apparatus for detecting foreign matter present on a photomask or a reticle for the manufacture of large-scale integrated circuits (LSI), said apparatus being provided with a mechanism for preventing unnecessary so-called stray light generated when the laser beam is incident thereon.

In an apparatus for detecting foreign matter present on such photomask or reticle, the detection can be achieved by scanning the specimen, for example, with a laser beam and converting the light scattered by the foreign matter into an electric signal by means of photoelectric converting means such as a photodiode or a photomultiplier.

When a specimen such as a photomask or a reticle is illuminated by a laser beam, foreign matter present on the specimen usually generates omnidirectional scattering while the edges of the circuit pattern, such as the edges of chromium masks, formed close on said specimen generates light scattering with directivity. Therefore, in order to distinguish the scattered light from such pattern edges, it is possible to provide plural photoelectric converting means in such positions as to inspect the area illuminated by the laser beam from different angles and to identify the presence of foreign matter only when all photoelectric converting means receive any scattered light.

In such inspection apparatus, the time required for inspection and the accuracy of detection depend on whether the specimen is perpendicularly or obliquely illuminated by the laser beam. For example, the inspection can be carried out within a relatively short time if the specimen is scanned by an oblique incident laser beam. However, in case a glass-based specimen, such as a photomask or a reticle, receives an oblique laser beam at a certain angle, a part of said laser beam travels inside the glass plate and again emerges therefrom as a stray light. This phenomenon will be further explained later, but the afore-mentioned photoelectric converting means may receive said stray light. Also the laser beam directed to the photomask or reticle is often reflected at the incident surface or is transmitted through a transparent area outside the circuit pattern, and such reflected or transmitted laser light is further reflected or scattered in the inspecting apparatus to generate stray light. Such stray light, being approximately equal to or often stronger, in intensity, than the scattered light from the foreign matter, reduces the ability of foreign matter detection and eventually leads to an erroneous detection.

SUMMARY OF THE INVENTION

The principal object of the present invention is to provide an apparatus capable of detecting foreign matter on a specimen with a high accuracy.

The above-mentioned object can be achieved according to the present invention by an apparatus comprising means for scanning the surface of the specimen with an oblique incident light beam, means for photoelectrically detecting the scattered light generated in the trajectory of said light beam scanning on said specimen, and means for eliminating stray light unnecessary for the foreign matter detection.

In a preferred embodiment of the present invention, said means for eliminating stray light comprises means for absorbing the light normally reflected of transmitted by the specimen, and stray light shielding means positioned in the vicinity of the photoelectric detecting means.

DESCRIPTION OF THE PREFERRED EMBODIMENTS

Figure 1:
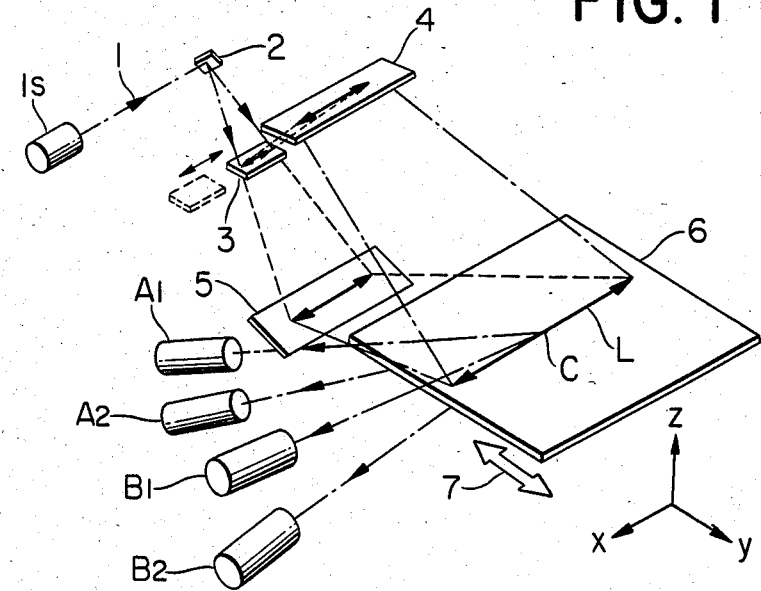
FIG. 1 is a perspective view showing the basic structure for foreign matter detection according to the present invention.

Now referring to FIG. 1 showing the basic structure for foreign matter detection according to the present invention, a laser beam 1 generated from a laser source ls is deflected with vibration by a scanner 2. The vibrating laser beam 1 is reflected by a movable mirror 3 for switching over the optical path, then reflected by a fixed mirror 4 and obliquely enters the upper surface of a specimen 6 such as a photomask or a reticle.

It is assumed that the mask 6 extends along the x-y plane in an x,y,z-coordinate system and that the trajectory L of the laser beam 1 scanning on said mask 6 extends in the direction of x-axis across the pattern area of the mask 6. Also it is assumed that the mask 6 is rendered movable, by an unshown driving mechanism, in the direction of y-axis as shown by an arrow 7 along the x-y plane.

The above-mentioned movable mirror 3 can be retracted, from the path of the vibrating laser beam 1 emitted by the scanner 2, in a direction parallel to the x-y plane to the broken-lined position shown in FIG. 1. In such retracted state of the movable mirror 3, the laser beam 1 from the scanner 2 is reflected by a movable mirror 5 and obliquely enters the lower surface of the mask 6 to scan it.

Such oblique entry of the laser beam 1 onto the upper or lower surface of the mask 6 provides a larger exposure area on the mask 6 than in the case of perpendicular entry of the laser beam, thereby reducing the time required for scanning with the laser beam, i.e. the time required for inspection. Also such oblique entry of the laser beam 1 allows clearer separation the direction of light scattered by the pattern edges from the direction of light scattered by the foreign matters. Also a space present above the trajectory L of the laser beam 1 can be utilized for placing an observing optical system such as a microscope for visual observation of the detected foreign matter. In consideration of the foregoing, the laser beam 1 is desirably so positioned as to enter the upper or lower surface of the mask 6 with an angle of 10°–30°, or an incident angle of 80°–60°.

Two photoelectric converting means A1, B1, each comprising a lens for collecting the scattered light from the trajectory L and a photodiode or a photomultiplier for converting the intensity of the collected scattered light into an electric signal, are so positioned as to observe the center C of said trajectory L from different angles.

The optical axis of the lens in said photoelectric converting means B1 passes through said center C and crosses the upper surface of the mask 6, i.e. the x-y plane with a small angle thereto, for example in a range of 10°–30°. Said optical axis is furthermore so positioned as to observe said trajectory L from the perpendicular direction, namely as to be parallel to the x-z plane. On the other hand, the optical axis of the lens of the photoelectric converting means A1 passes through the center C of the trajectory L, thus crossing the upper surface of the mask 6 with a small angle thereto, for example in a range of 10°–30°, and is so positioned as to form an angle in the range of 30°–60° with the optical axis of the photoelectric converting means B1 or with the trajectory L. Said converting means A1 and B1 are positioned at a same distance from the center C.

With such arrangement of the converting means A1, B1 and in case the circuit pattern is present on the upper surface of the mask 6 receiving the laser beam 1, a foreign matter present on the trajectory L would induce substantially equal electric signals simultaneously in both converting means A1, B1. On the other hand, in case the laser beam 1 illuminates an edge on the trajectory L, the converting means A1, B1 generate different electric signals due to the directivity of the light scattered by said edge. It is therefore possible to identify, by comparing the electric signals from the converting means A1, B1, whether the scattered light coming from the trajectory L is caused by foreign matter or by a pattern edge.

Such method of foreign matter detection is however unable to identify whether said foreign matter is present on the upper or lower surface of the mask 6. More specifically, the laser beam 1 passing through a transparent area of the mask 6 is also scattered by foreign matter present on the lower surface of the mask 6, and the scattered light again passes through the transparent area of the mask 6 and enters the converting means A1 and B1. In this manner the above-described method is defective in that it is unable to distinguish the foreign matter present on the upper surface of the mask 6 from that on the lower surface thereof.

It is also to be noted that a foreign matter present on an opaque area, for example chromium layer, of the circuit pattern does not affect a pattern printed on the silicon wafer with said mask. It is therefore possible to significantly improve the efficiency of the inspection if the foreign matter present on the transparent area is distinguished from that on the circuit pattern and the foreign matter on the transparent area alone detected. In order to achieve this objective, there are additionally provided photoelectric converting means A2, B2 as shown in FIG. 1, which are positioned symmetric to the converting means A1, B1 with respect to the x-y plane containing the upper or lower surface of the mask 6. Each of said converting means A2, B2 comprises a lens and a photodiode or a photomultiplier in the same manner as in the converting means A1, B1, and the optical axis of said converting means A2 or B2 passes through the center C of the trajectory L from the lower side of the mask 6, with such light-receiving angle being set as to collect the light scattered downwards on the trajectory L.

Inspection identifying the state of foreign matter is thus rendered possible by detecting the scattered light present under the mask 6 with the converting means A2, B2 and comparing the corresponding signals with those obtained from the converting means A1, B1.

Figure 2:
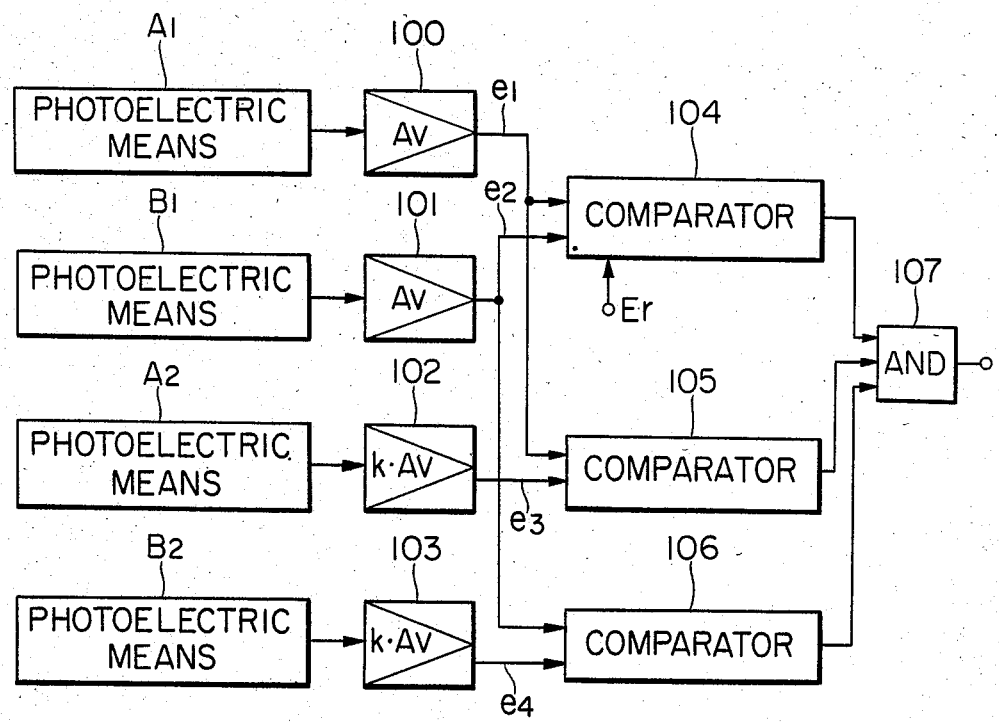
FIG. 2 is a block diagram of a circuit for processing the detected electric signals.

The detection signals obtained from the aforementioned photoelectric converting means A1, B1, A2, B2 are processed in a electrical circuit means shown in FIG. 2. It is assumed that said converting means A1, B1, A2, B2 generate electric signals of the same intensity in response to the same light intensity, and that the movable mirror 3 is inserted in the light path of the vibrating laser beam 1. Referring to FIG. 2, the detection signals from the converting means A1, B1 for observing a mask surface receiving the laser beam are respectively amplified, by a factor AV, by amplifiers 100, 101, while the detection signals from the converting means A2, B2 are respectively amplified, by a factor KAV, by amplifiers 102 and 103. The output signals e1, e2 from said amplifiers 100, 101 are supplied to a comparator 104, which compares said signals e1 and e2 with a reference voltage Er and generates a logic signal, for example "1", only when said signals e1, e2 are both larger than said reference voltage Er. Said signal e1 and the output signal e3 from the amplifier 102 are supplied to a comparator 105, which produces a logic signal, for example "1", only in case of e1>e3. Similarly the signal e2 and the output signal e4 from the amplifier 103 are supplied to a comparator 106, which produces a logic signal, for example "1", only in case of e2>e4. The output signals from said comparators 104, 105, 106 are supplied to an AND gate 107, which generates a logic signal "1" indicating the detection of foreign matter only when said output signals are all "1".

The above-mentioned reference voltage Er is determined in consideration of various factors, including the distance of the converting means A1, B1 from the center C, the converting efficiency of the photodiodes or photomultipliers, the amplifying factor AV of the amplifiers 100, 101, etc. and also in relation to the dimension of the foreign matter. Since the intensity of the scattered light is dependent on the dimension of the foreign matter, said reference voltage Er should be determined in consideration of the minimum dimension of the foreign matter to be detected. Stated differently, the sensitivity of the foreign matter detection is determined by the magnitude of said reference voltage Er.

In the above-described circuit, the amplifying factor KAV of the amplifiers 102, 103 is determined in the following manner. It is now assumed that foreign matter is present in a transparent area at the center C of the trajectory L. When it is illuminated by the laser beam 1, the intensity of the scattered light, transmitted downwards through the transparent area and received by the converting means A2, B2, is about $\Delta - \frac{1}{8}$ of that of the scattered light received by the converting means A1, B1. On the other hand, in case foreign matter present at the center C on the opposite lower surface is illuminated by the laser beam 1 transmitted through the transparent area of the mask at the center C, the intensity of the scattered light, generated by said foreign matter and received by the converting means A2, B2, is larger than that of the scattered light received by the converting means A1, B1. Furthermore, in case the laser beam 1 illuminates a pattern edge on the trajectory L, the intensity of the scattered light resulting from said edge is approximately the same above and below the mask, so that the converting means A1 and A2, or B1 and B2 provide approximately same detection signals. In consideration of the foregoing, the constant k is selected on the order of 1.5 to 3, in order to only detect the foreign matter present in a transparent area of the upper surface receiving the laser beam. It is to be noted that the signals e1, e2 may both exceed the reference voltage Er when the laser beam 1 illuminates a pattern edge, due to the directivity of the light scattered from said edge. In such case the comparator 104 provides a logic signal "1". However, the converting means A1 and A2, or B1 and B2 provide approximately equal detection signals in such case, so that, with the constant k selected in the range of 1.5 to 3 as explained above, relations $e1 < e3$ and $e2 < e4$ are attained to provide logic signals "0" from the comparators 105, 106, and thus a logic signal "0" from the AND gate 107. In this manner, by the selection of the constant k in the range of 1.5 to 3, it is rendered possible to avoid erroneous identification of the scattered light from an edge as that from foreign matter. Only in case the foreign matter is present on the upper surface receiving the laser beam, relations $e1 > e3$ and $e2 > e4$ are attained and the signal e1, e2 both exceed the reference voltage Er to provide a logic signal "1" from the AND gate 107 indicating the detection of foreign matter.

Also the circuit shown in FIG. 2 can be further provided with a comparator providing a logic signal "0" from the AND gate 107 in case the detection signal from the converting means A1 or B1 is far larger, for example in excess of 8 times, than that from the converting means A2 or B2, corresponding to a case that foreign matter is present on an opaque area of the mask 6.

In this manner, the comparison of the intensities of the scattered lights above and below the mask 6 enables extremely exact inspection, identifying whether the foreign matter is present on the upper or lower surface of the mask 6 and in a transparent area or an opaque area thereof. Besides the apparatus shown in FIGS. 1 and 2 is capable of detecting foreign matter present on the lower surface alone of the mask 6 by simply retracting the aforementioned movable mirror 3. For this purpose the connections between the converting means A1, A2 and the corresponding amplifiers as well as those between B1, B2 and the corresponding amplifiers are switched over and the reference voltage Er is adjusted in response to the retracting movement of the movable mirror 3. In this manner the apparatus of the present invention is capable of detecting the foreign matter present on both surfaces of the mask 6 within a very short time only by the displacement of the movable mirror 3, without inverting the mask 6.

Figure 3:
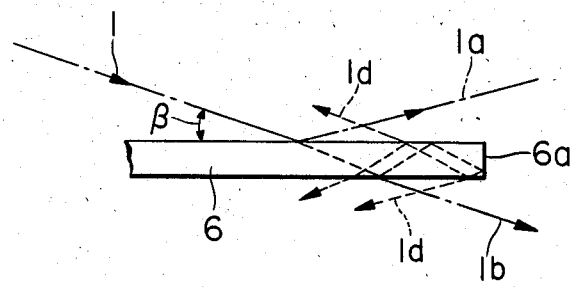
FIG. 3 is a cross-sectional lateral view showing the principle of stray light generation.
Figure 4:
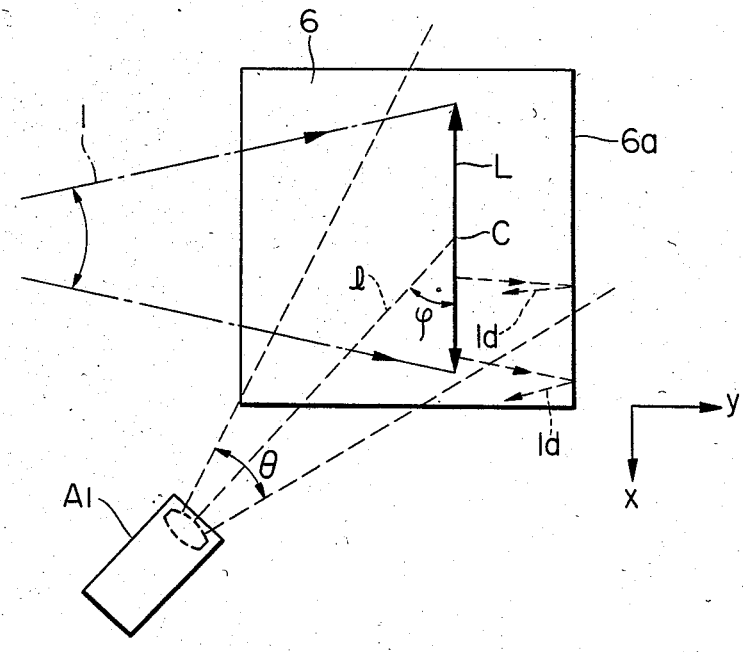
FIG. 4 is a plan view showing the principle of stray light generation.

The aforementioned stray light may be generated by two causes in the detection of foreign matter by illuminating a specimen utilizing a transparent substrate, such as a parallel-faced glass plate as in the photomask 6, with a light beam with a high energy density such as the laser beam 1. Firstly, the stray light may be generated by the reflection or scattering in the apparatus of the laser beam normally reflected or transmitted by the mask. As shown in FIG. 3, a part of the laser beam 1 entering the upper surface of the mask 6 with an angle $\beta$ proceeds as a normal reflection 1a, and, if the circuit pattern is not present at the beam incident point, another part proceeds as a transmission 1b through the mask 6. The intensities of said normal reflection 1a and transmission 1b depend on the angle $\beta$ between the laser beam 1 and the mask 6, but such normal reflection 1a and/or transmission 1b is always present and eventually reflected or scattered in the apparatus to give rise to the stray light affecting the photoelectric converting means. Secondly, said stray light may be generated from the oblique entry of the laser beam 1 into the mask 6. Again as shown in FIG. 3, a part of the laser beam 1 entering a transparent area of the mask 6 proceeds in the interior of the transparent substrate of the mask 6 with repeated reflections to an end face 6a of said substrate, where the light is totally reflected to form light beam 1d emerging from the upper and lower surfaces of the mask 6. Said beam 1d is strongest at the upper and lower surfaces close to the end face 6a, and, returning toward the direction of the laser beam source, is apt to be received as the stray light by the converting means A1 observing the trajectory L on the mask 6 from the incident side of the laser beam 1. When the laser beam 1, as shown in FIG. 4, is obliquely incident on and scans the mask 6, the optical axis l of the lens of the converting means A1 is directed toward the center C of the scanning trajectory L of the oblique laser beam 1 as shown in FIG. 4, and the angle $\phi$ between said trajectory L and the optical axis l is selected in a range of 30° to 60° as explained in the foregoing. Also said converting means A1 has to receive the scattered light not only generated at the center C but also at any point along the trajectory L. Therefore, a light-receiving angle $\theta$ so selected as to cover the entire trajectory L on the x-y plane of the x,y,z-coordinate system will naturally cover the end face 6a. When the mask 6 is scanned by the laser beam 1 under such condition, the light 1d, which proceeds inside the mask 6, is normally reflected at the end face 6a and emerges from the upper surface of the mask, reaches the converting means A1 and becomes stronger as the trajectory L approaches the end face 6a.

Figure 5:
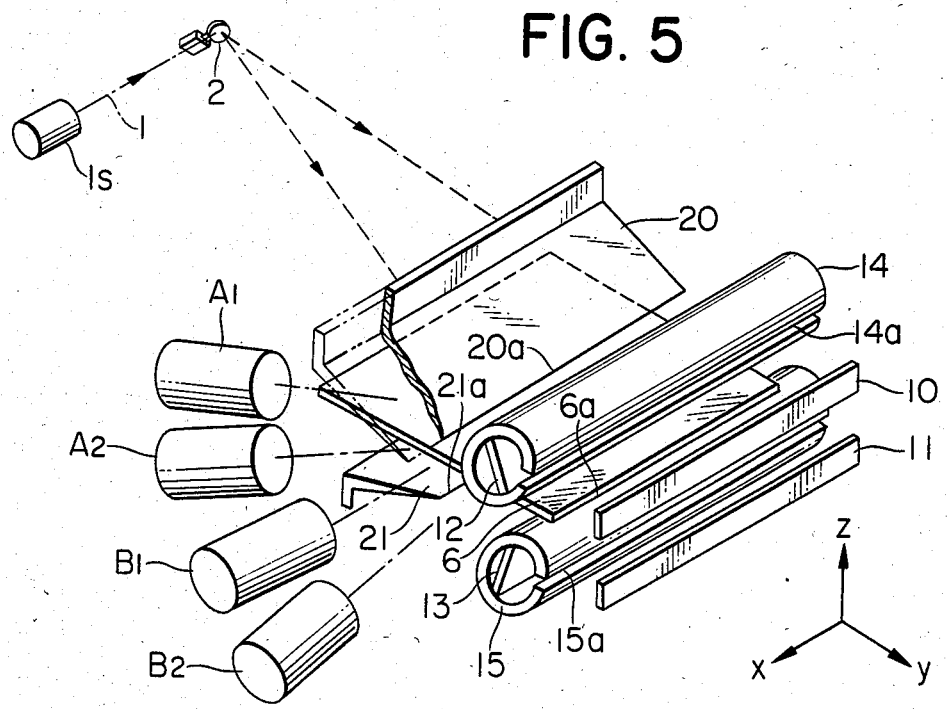
FIG. 5 is a perspective view of an apparatus embodying the present invention.
Figure 6:
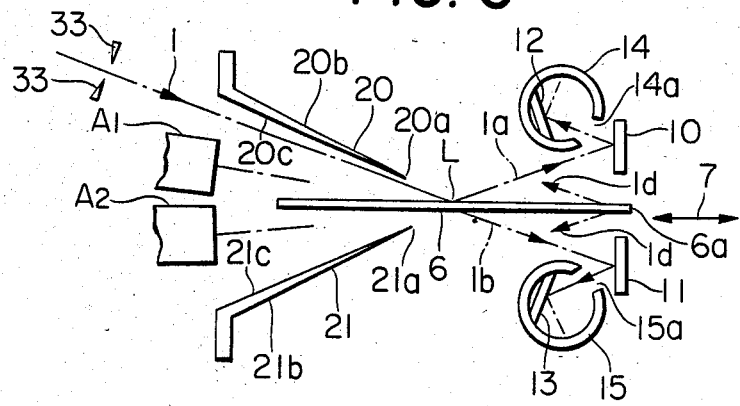
FIG. 6 is a side view of the apparatus shown in FIG. 5.

In order to avoid such stray light, the apparatus of the present invention is provided with a preventive mechanism as shown in FIGS. 5 and 6.

In FIGS. 5 and 6, the laser beam 1, scanner 2, mask 6 and photoelectric converting means A1, A2, B1, B2 are positioned in the same manner as in FIG. 1, while the movable mirror 3 and fixed mirrors 4, 5 are omitted for the purpose of simplicity, and the entire apparatus is housed in a light-tight casing which shields outer light.

On the path of the normal reflection 1a from the trajectory L on the mask there is provided an optical member 10, comprising an optical surface facing the incoming direction of the laser beam. Said optical surface is substantially perpendicular to the surface of the mask 6 or the x-y plane and substantially parallel to the trajectory L, and has a length sufficiently covering the length of the trajectory L. The optical surface of said optical member 10 is composed of a material absorbing the major portion of the laser beam without transmission and with a small normal-reflection thereon. Also on the path of the transmitted light 1b provided is an optical member 11 of the same material and shape as the optical member 10. In opposed relationship to the optical surfaces of said optical members 10, 11 there are respectively provided light absorbing members 14, 15 composed of cylinders parallel to said optical members 10, 11. Said cylinders are provided with slots 14a, 15a along a generatrix thereof in order to receive the light reflected from the optical members 10, 11, and are internally provided with plate members 12, 13, alongside said slots 14a, 15a, capable of absorbing a major portion of the incoming light and reflecting only a small portion thereof. Said plate members 12, 13 are so positioned as to reflect the incoming light toward the interior of the absorbing members 14, 15.

Preferably the internal wall of the absorbing members 14, 15 is so treated as to cause substantially complete scattering. Also the width of the slot 14a or 15a is preferably selected as small as possible, on the condition that the laser beam reflected by the optical member 10 or 11 does not fall on the end faces or the edges of said slots 14a or 15a. Furthermore, the external wall of the absorbing members 14, 15 is preferably formed as a low-reflecting surface, which absorbs the incoming light without reflection.

Furthermore, in order to intercept the light 1d totally reflected at the end face 6a of the mask 6, there are provided two light shield plates 20, 21 on both sides of the mask 6. Said light shield plates 20, 21 are so positioned as to intercept the light 1d proceeding toward the converting means A1, A2 but are not effective for the converting means B1, B2 observing the trajectory L from the perpendicular direction, since said light 1d only affects the converting means A1 and A2. Said light shield plates 20, 21 are positioned symmetric to the mask 6 and with a sloping angle thereto, and said angle is so determined that said plates are as close as possible to but not obstructing the path of the laser beam 1. More specifically, the light shield plate 20 is positioned with an angle of 10° to 30° in the positive direction of the z-axis from the x-y plane, and the light shield plate 21 is positioned with an angle of 10° to 30° in the negative direction of the z-axis from the x-y plane, said angle being however selected slightly larger than the angle between the laser beam 1 and the mask 6. The edges 20a, 21a of said plates 20, 21 are positioned close to and substantially parallel to the trajectory L on the mask 6, and are long at least enough to cover the light-receiving angle θ of the converting means A1, A2 indicated by dotted lines in FIG. 4. Furthermore, said edges 20a, 21a of the light shield plates 20, 21 are preferably pointed to a sharp angle, so that they can be positioned very close to the optical path of the laser beam 1.

As illustrated in FIG. 6, the edges 20a, 21a of the light shield plates 20, 21 cannot be extended to the trajectory L, since the converting means B1, B2 are positioned also to receive the light scattered from the trajectory L, although they are not shown in FIG. 6. However, if said converting means B1, B2 are positioned symmetrical to the converting means A1, A2 with respect to a plane passing through the center C of the trajectory L and parallel to the y-z plane, the light shield plates 20, 21 may be positioned for example along the x-z plane including the trajectory L of the laser beam 1. Naturally the edges 20a, 20b have to be as close as possible to the mask 6 also in this case. The external faces 20b, 21b of said light shield plates are composed of a low-reflecting material which does not scatter the incoming light but causes only a little normal reflection.

The internal faces 20c, 21c of said light shield plates are also composed of a low-reflecting and non-scattering material which absorbs the substantial part of the incoming light and normally reflects the remainder, in order to avoid light scattering in case the slight broadening of the laser beam 1 eventually falls on said internal faces, since such light scattering by the internal faces will affect the converting means A1, A2.

Also it is conceivable to limit the broadening of the laser beam itself in order that the internal faces 20c, 21c are not illuminated by such broadened laser beam. For this purpose, as shown in FIG. 6, a stopper plate 33 having a slit in the scanning direction may be provided on the optical path of the laser beam 1 between the unshown condenser lens behind the scanner 2 and the light shield plates 20, 21. Said stopper plate 33 does not limit the laser beam in the scanning direction thereof but suppresses the broadening of the beam in the perpendicular direction. The width of said slit may be so determined, for example, as to cut off the laser beam at a position where the beam intensity decreases to $1/e^2$ (e is the base of natural logarithm) in case the beam intensity shows Gaussian distribution.

The above-described light absorbing means and intercepting means have the following effects on the stray light. The laser beam 1 obliquely entering the mask 6 is divided into the normal reflection 1a and the transmission 1b which respectively arrive at the optical members 10, 11. Said members absorb most of said normal reflection 1a and transmission 1b and reflect only several percent thereof to the light trapping members 14, 15, in which the incoming lights are mostly absorbed by plate members 12, 13 and the remaining lights of several percent are reflected and guided to the internal walls of the trapping members 14, 15. The laser beams are scattered on said internal walls but the scattered lights emerging from the slots 14a, 15a are far weaker than the lights scattered by the foreign matter or by the pattern edges. In this manner the stray lights resulting from the normal reflection 1a and the transmission 1b are not detected by the converting means A1, A2, B1, B2.

On the other hand, the light beams 1d reflected at the end face 6a of the mask 6 and emerging from the upper and lower surfaces thereof reach the external faces 20a, 20b of the light shield plates 20, 21 Consequently said light beams 1d are mostly absorbed by said external faces 20b, 21b and do not reach the converting means A1, A2. Also the detecting function of the converting means B1, B2 are not affected.

In the foregoing embodiments, the optical members 10, 11 can be easily and unexpensively composed for example of colored glass filters or neutral density filters, capable of absorbing the wavelength region of the laser beam and having an evaporated anti-reflection layer thereon. The plate members 12, 13, trapping members 14, 15 and light shield plates 20, 21 may be composed of the same material as the optical members 10, 11 but can also be formed of a metal plate such as an aluminum alloy with a lustrous black alumite painting thereon. Also the internal wall of the trapping members 14, 15 can be formed simply by a black matted painting.

Figure 7:
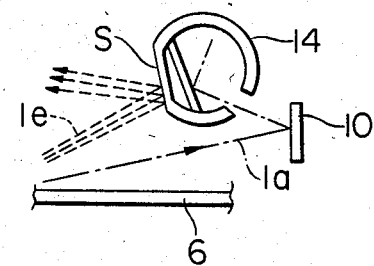
FIG. 7 is a side view of an apparatus constituting another embodiment of the present invention.

As clearly shown in FIG. 6, the trapping members 14, 15 are so positioned that the external walls thereof do not receive the normal reflection 1a nor the transmission 1b, but they may receive the light scattered from the circuit pattern edges on the trajectory L, so that the converting means A1, A2 may receive the scattered light reflected by the external walls of said trapping members 14, 15. In order to avoid such reflected light, the cylindrical trapping members 14, 15 may be provided with a flat area on a part of the external wall as shown in FIG. 7, thereby absorbing most of the scattered light 1e from the pattern edge and reflecting further away from the mask 6. A more complete prevention of the stray light can be achieved in this manner. The reflected light from said flat area S can be conveniently guided toward the external face 20b of the light shield plate 20.

We claim:

1. An apparatus for detecting foreign matter present on a planar substrate comprising:
   (a) irradiating means for generating a light beam obliquely entering one surface of said substrate and including scanning means for causing said light beam to scan said surface;
   (b) discriminating means which includes photoelectric converting means so positioned as to receive a part of the light scattered from said foreign matter and adapted to generate electric output signals corresponding to the intensity of the received light, and to identify the presence of said foreign matter in response to said electric output signals; and
   (c) absorbing means positioned on the optical path of the light beam regularly reflected by said surface and adapted to absorb said regularly reflected light beam, said absorbing means including a regular reflector member having a light absorbing property with respect to said light beam and which is positioned across the optical path of said regularly reflected light beam, and an optical trap member which is positioned opposite to said regular reflector member and which is used to absorb said regularly reflected light beam regularly reflected by said regular reflector member.

2. A foreign matter detecting apparatus according to claim 1, wherein each of said regular reflector member and said optical trap member is positioned along the scanning direction of said light beam and has a dimension sufficiently covering the range of the optical path of said regularly reflected light beam displaced by said scanning.

3. A foreign matter detecting apparatus according to claim 1, wherein said photoelectric converting means is positioned in a space of the incident side with respect to the entering position of said scanning light beam, and further includes light sheild means positioned between said space of the incident side containing the optical path of said entering light beam as well as said photoelectric converting means, and a space at the opposite side.

4. A foreign matter detecting apparatus according to claim 1, further comprising a light shield member of plate-form having an edge extending parallel to said surface of said substrate adjacent to the surface of the substrate.

5. A foreign matter detecting apparatus according to claim 4, wherein said light shield member is positioned obliquely to said surface of said substrate and substantially parallel to the optical path of said entering light beam.

6. An apparatus for detecting foreign matter present on a planar substrate having a light-transmitting property, comprising:
   (a) irradiating means for generating a light beam obliquely entering one surface of said substrate and including scanning means for causing said light beam to scan said surface;
   (b) discriminating means which includes photoelectric converting means so positioned as to receive a part of the light scattered from said foreign matter and adapted to generate electric output signals corresponding to the intensity of the received light, and to identify the presence of said foreign matter in response to said electric output signals; and
   (c) absorbing means positioned on the optical path of the light beam transmitted by said substrate and emerging from the outer surface thereof and adapted to absorb said transmitted light beam, said absorbing means including a regular reflector member having a light absorbing property property with respect to said light beam and which is positioned across the optical path of said transmitted light beam, and an optical trap member which is positioned opposite to said regular reflector member and which is used to absorb said transmitted light beam regularly reflected by said regular reflector member.

7. A foreign matter detecting apparatus according to claim 6, wherein said photoelectric converting means is positioned in a space of the incident side with respect to the entering position of said scanning light beam, and further includes light shield means positioned between said space of the incident side containing the optical path of said entering light beam as well as said photoelectric converting means, and a space at the opposite side.

8. A foreign matter detecting apparatus according to claim 6, wherein each of said regular reflector member and said optical trap member is positioned along the scanning direction of said light beam and has a dimension sufficiently covering the range of the optical path of said transmitted light beam displaced by said scanning.

9. A foregoing matter detecting apparatus according to claim 6, further comprising a light sheild member of plate-form having an edge extending parallel to the other surface of said substrate adjacent to the other surface of the substrate.

* * * * *

UNITED STATES PATENT AND TRADEMARK OFFICE
CERTIFICATE OF CORRECTION

PATENT NO. : 4,568,835
DATED     : February 4, 1986
INVENTOR(S) : KAZUNORI IMAMURA, ET AL.

It is certified that error appears in the above-identified patent and that said Letters Patent is hereby corrected as shown below:

Column 4, line 60, change "$\Delta - 1/8$" to --$1/3 - 1/8$--.

Column 10, line 48 (Claim 9, line 1), change "foregoing" to --foreign--.

Signed and Sealed this

Twenty-ninth Day of April 1986

[SEAL]

Attest:

DONALD J. QUIGG

Attesting Officer

Commissioner of Patents and Trademarks